United States Patent
Parker et al.

(10) Patent No.: US 10,215,827 B2
(45) Date of Patent: Feb. 26, 2019

(54) METHOD TO MEASURE TISSUE TEXTURE USING NMR SPECTROSCOPY TO IDENTIFY THE CHEMICAL SPECIES OF COMPONENT TEXTURAL ELEMENTS IN A TARGETED REGION OF TISSUE

(71) Applicant: BIOPROTONICS, LLC, Santa Ynez, CA (US)

(72) Inventors: Ian Parker, Santa Barbara, CA (US); David R. Chase, Santa Barbara, CA (US); Timothy W. James, Santa Barbara, CA (US); Kristin James, Santa Barbara, CA (US)

(73) Assignee: BIOPROTONICS INC., Santa Ynez, CA (US)

( * ) Notice: Subject to any disclaimer, the term of this patent is extended or adjusted under 35 U.S.C. 154(b) by 0 days.

(21) Appl. No.: 16/028,768

(22) Filed: Jul. 6, 2018

(65) Prior Publication Data

US 2018/0313925 A1 Nov. 1, 2018

Related U.S. Application Data

(63) Continuation-in-part of application No. 15/604,465, filed on May 24, 2017, now Pat. No. 10,061,003, (Continued)

(51) Int. Cl.
*G01R 33/56* (2006.01)
*G01R 33/48* (2006.01)
(Continued)

(52) U.S. Cl.
CPC ..... *G01R 33/5601* (2013.01); *G01R 33/4818* (2013.01); *G01R 33/4835* (2013.01);
(Continued)

(58) Field of Classification Search
CPC ............ G01R 33/5601; G01R 33/4818; G01R 33/4835; G01R 33/5602; G01R 33/5616;
(Continued)

(56) References Cited

U.S. PATENT DOCUMENTS 9,366,738 B2 * 6/2016 Chase ................ G01R 33/4818
9,664,759 B2 * 5/2017 James .................. G01R 33/381
(Continued)

*Primary Examiner* — Dixomara Vargas
(74) *Attorney, Agent, or Firm* — Felix L. Fischer

(57) ABSTRACT

A method for identifying the chemical species of various textural elements in a targeted region of tissue wherein a volume of interest (VOI) is selectively excited and a k-encode gradient pulse is applied to induce phase wrap to create a spatial encode for a specific k-value and orientation. The specific k-value is selected based on anticipated texture within the VOI. Multiple sequential samples of the NMR RF signal encoded with the specific k-value are recorded as signal data. The Fourier Transform of the acquired signal data is then taken, wherein for each k-encode, the signal recorded is indicative of the spatial frequency power density at that point in k-space. Each peak in the NMR spectrum is then evaluated, whereby the relative contribution to the texture of tissue in the VOI at a k-value for each chemical species is determined.

17 Claims, 8 Drawing Sheets

Related U.S. Application Data which is a continuation-in-part of application No. 15/288,974, filed on Oct. 7, 2016, now Pat. No. 9,664,760, which is a continuation-in-part of application No. 15/167,828, filed on May 27, 2016, now Pat. No. 9,664,759, which is a continuation-in-part of application No. 14/840,327, filed on Aug. 31, 2015, now Pat. No. 9,366,738.

(60) Provisional application No. 62/044,321, filed on Sep. 1, 2014, provisional application No. 62/064,206, filed on Oct. 15, 2014, provisional application No. 62/107,465, filed on Jan. 25, 2015, provisional application No. 62/302,577, filed on Mar. 2, 2016, provisional application No. 62/238,121, filed on Oct. 7, 2015, provisional application No. 62/382,695, filed on Sep. 1, 2016, provisional application No. 62/529,104, filed on Jul. 6, 2017, provisional application No. 62/635,349, filed on Feb. 26, 2018.

(51) Int. Cl.
*G01R 33/483* (2006.01)
*G01R 33/561* (2006.01)
*G01R 33/563* (2006.01)
*G06T 7/00* (2017.01)

(52) U.S. Cl.
CPC ..... *G01R 33/5602* (2013.01); *G01R 33/5616* (2013.01); *G01R 33/5619* (2013.01); *G01R 33/56341* (2013.01); *G06T 7/0012* (2013.01); *G06T 2207/10088* (2013.01)

(58) Field of Classification Search
CPC .......... G01R 33/56341; G01R 33/5619; G06T 7/0012; G06T 2207/10088
See application file for complete search history.

(56) References Cited

U.S. PATENT DOCUMENTS

| | | | |
|---|---|---|---|
| 9,664,760 B2 * | 5/2017 | James | G01R 33/4818 |
| 10,061,003 B2 * | 8/2018 | James | A61B 5/055 |
| 2013/0221961 A1 * | 8/2013 | Liu | G01R 33/56545 |
| | | | 324/307 |
| 2016/0061917 A1 * | 3/2016 | Chase | G01R 33/4818 |
| | | | 324/309 |
| 2016/0274203 A1 * | 9/2016 | James | G01R 33/381 |
| 2017/0030986 A1 * | 2/2017 | James | G01R 33/4818 |
| 2017/0261584 A1 * | 9/2017 | James | A61B 5/055 |

* cited by examiner

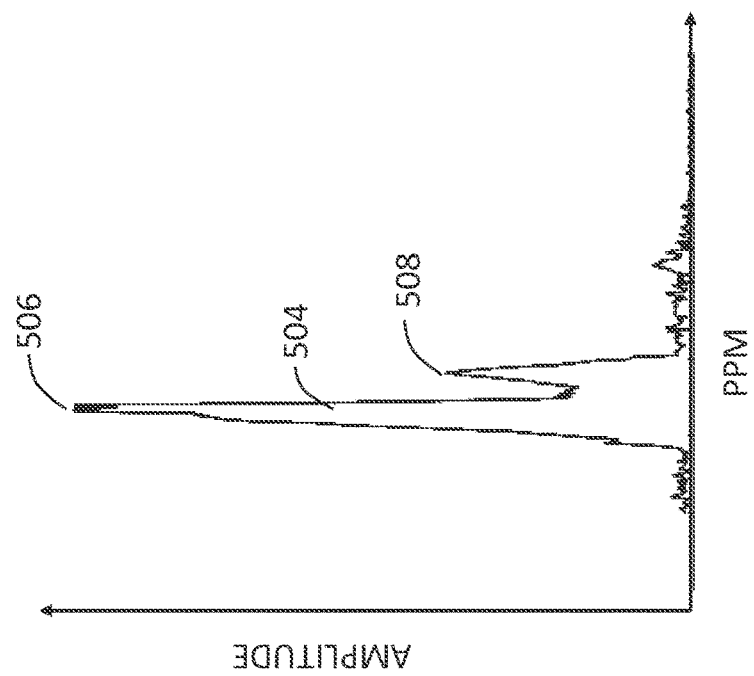
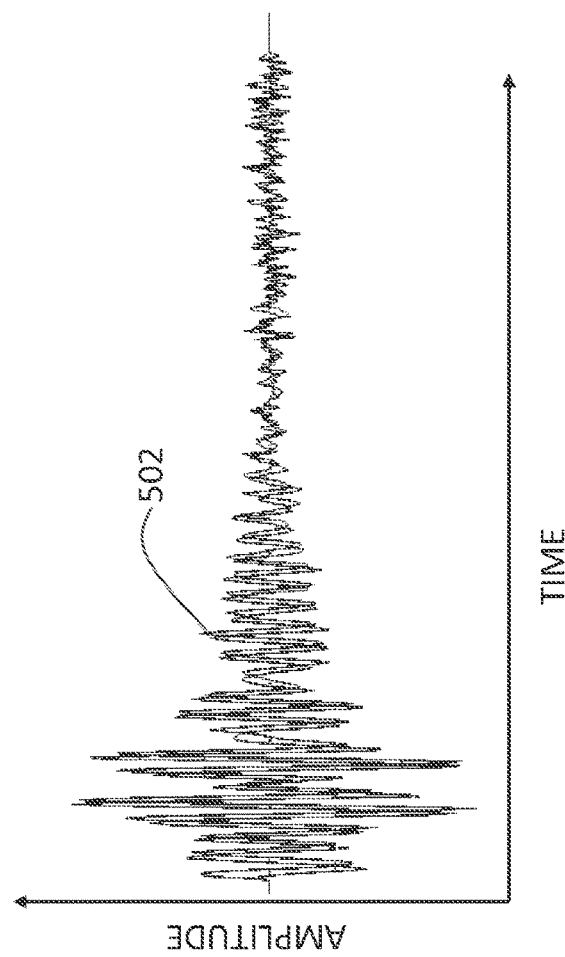
FIG. 5b
FIG. 5a

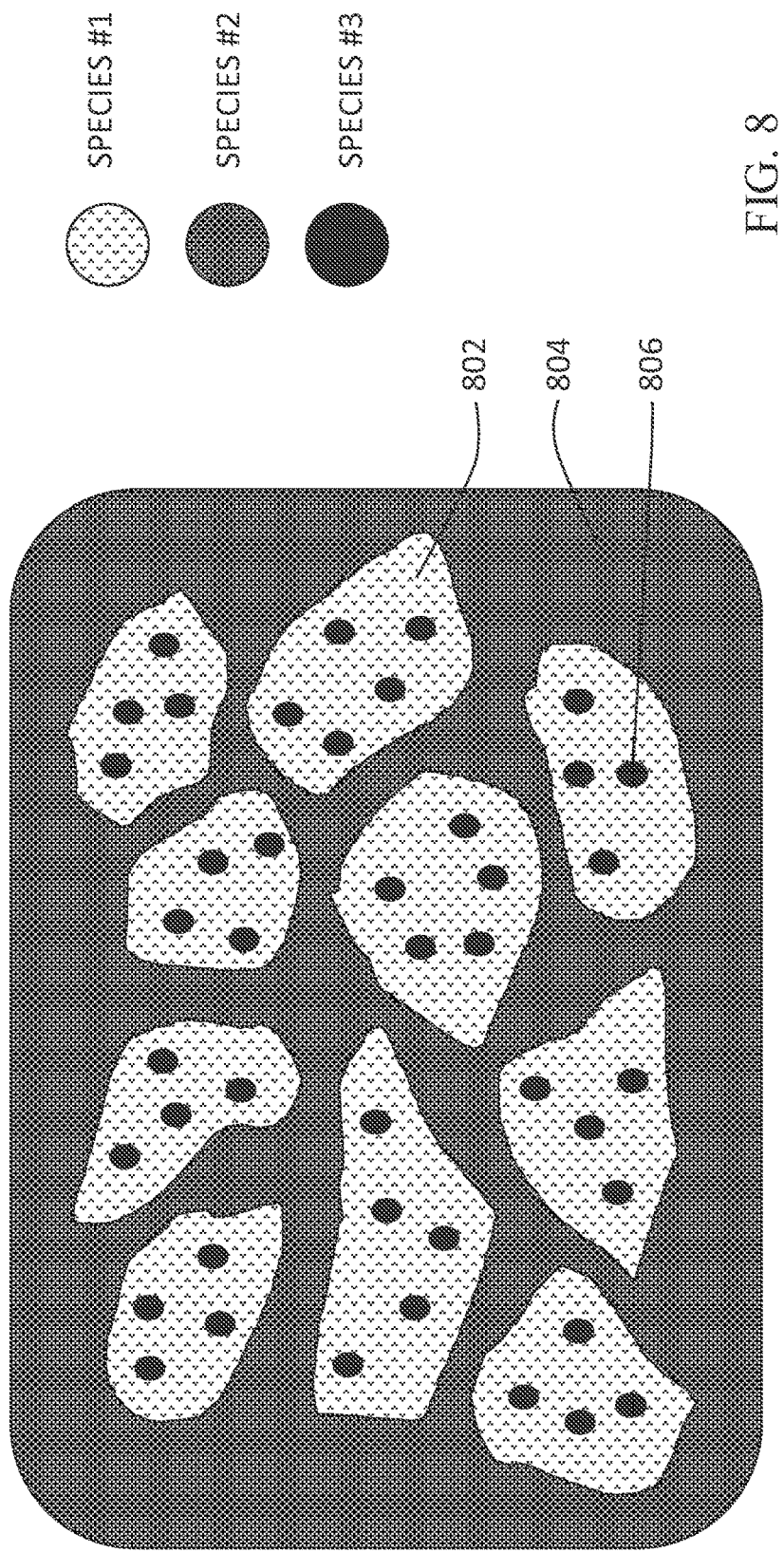

METHOD TO MEASURE TISSUE TEXTURE USING NMR SPECTROSCOPY TO IDENTIFY THE CHEMICAL SPECIES OF COMPONENT TEXTURAL ELEMENTS IN A TARGETED REGION OF TISSUE

REFERENCES TO RELATED APPLICATIONS

This application is a continuation-in-part of application Ser. No. 15/604,465 filed on May 24, 2017 entitled SELECTIVE SAMPLING FOR ASSESSING STRUCTURAL SPATIAL FREQUENCIES WITH SPECIFIC CONTRAST which is a continuation-in-part of application Ser. No. 15/288,974 filed on Oct. 7, 2016, now U.S. Pat. No. 9,665,760, which is a continuation in part of Ser. No. 15/167,828 filed on May 27, 2016, now U.S. Pat. No. 9,664,759, which is a continuation in part of application Ser. No. 14/840,327 filed on Aug. 31, 2015, now U.S. Pat. No. 9,366,738. Application Ser. No. 14/840,327 relies on the priority of U.S. provisional applications Ser. No. 62/044,321 filed on Sep. 1, 2014 entitled SELECTIVE SAMPLING MAGNETIC RESONANCE-BASED METHOD FOR ASSESSING STRUCTURAL SPATIAL FREQUENCIES, Ser. No. 62/064,206 filed on Oct. 15, 2014 having the same title and Ser. No. 62/107,465 filed on Jan. 25, 2015 entitled MICRO-TEXTURE CHARACTERIZATION BY MRI, the disclosures of which are incorporate herein by reference. Application Ser. No. 15/167,828 additionally relies on the priority of provisional application Ser. No. 62/302,577 filed on Mar. 2, 2016 entitled METHOD FOR ASSESSING STRUCTURAL SPATIAL FREQUENCIES USING HYBRID SAMPLING WITH LOW OR INCREASED GRADIENT FOR ENHANCEMENT OF VERY LOW NOISE SELECTIVE SAMPLING WITH NO GRADIENT. Application Ser. No. 15/288,974 relies on the priority of U.S. provisional application Ser. No. 62/238,121 filed on Oct. 7, 2015 entitled SELECTIVE SAMPLING MAGNETIC RESONANCE-BASED METHOD FOR ASSESSING STRUCTURAL SPATIAL FREQUENCIES and provisional application Ser. No. 62/382,695 filed on Sep. 1, 2016 entitled SELECTIVE SAMPLING FOR ASSESSING STRUCTURAL SPATIAL FREQUENCIES WITH SPECIFIC CONTRAST MECHANISMS. The present application additionally relies on the priority of provisional application Ser. No. 62/529,104 filed on Jul. 6, 2017 and provisional application Ser. No. 62/635,349 filed on Feb. 26, 2018. The referenced applications all have a common assignee with the present application and the disclosures thereof are incorporated herein by reference.

BACKGROUND

Field

This application is directed to nuclear magnetic resonance (NMR) spectroscopy and more particularly to a method for texture measurement extended to enable chemical characterization of the targeted tissue texture, thus providing both chemical and spatial identification of the texture, for enhanced diagnostic sensitivity.

Related Art

Much nascent pathology goes undetected because the fine-scale biologic tissue texture changes attendant with disease onset and progression are outside the resolution capability of current clinical imaging techniques and are only accessible by biopsy in a limited set of organs.

Although Magnetic Resonance Imaging (MRI) is the diagnostic of choice in a wide range of pathologies due to its ability to provide tunable tissue contrast non-invasively and without use of ionizing radiation, resolution is limited by the need for spatial coherence, to enable image reconstruction, throughout the entire image data acquisition. Spatial coherence is limited by patient motion, a problem exacerbated at the resolutions needed to image fine tissue texture—the extended data matrix required increases acquisition time, hence increasing image blurring. Furthermore, use of reregistration techniques to correct for motion is not possible at high k-values due to low signal on individual measurements.

Early and accurate diagnosis is key to successful disease management. Though fine textural changes in biologic tissue have long been recognized as the earliest markers in a wide range of diseases, robust clinical assessment of fine texture remains elusive due to blurring caused by subject motion over the time required for image data acquisition. As a result, though clinical imaging provides much information on disease state, assessment of the fine changes in biologic tissue texture that would allow early stage monitoring of disease are outside the capability of current clinical imaging techniques (see e.g. Weller C. Cancer detection with MRI as effective as PET-CT scan but with zero radiation risks. Medical Daily, Feb. 18, 2014; Regev A, Berho M, Jeffers L J et al. Sampling error and intraobserver variation in liver biopsy in patients with chronic HCV infection. Am J Gastroenterol. 2002 October; 97(10):2614-8. DOI: 10.1111/j.1572-0241.2002.06038; Bedossa P, Dargère D, Paradis V. Sampling variability of liver fibrosis in chronic hepatitis C. Hepatology. 2003 December; 38(6):1449-57. DOI:10.1016/j.hep.2003.09.022; Van Thiel D H, Gavaler J S, Wright H, Tzakis A. Liver biopsy: Its safety and complications as seen at a liver transplant center. Transplantation, 1993 May; 55(5):1087-90; Havsteen I, Ohlhues A, Madsen K H, Nybing J D, Christensen H, Christensen A. Are Movement Artifacts in Magnetic Resonance Imaging a Real Problem?—A Narrative Review. Front Neurol. 2017; 8:232. doi:10.3389/fneur.2017.00232; Kim B S, Lee K R, Goh M J. New Imaging Strategies Using a Motion-Resistant Liver Sequence in Uncooperative Patients. BioMed Research International, Volume 2014 (2014), Article ID 142658,http://dx.doi.org/10.1155/2014/142658).

This is a serious diagnostic shortcoming as extensive histology studies indicate clear correlation between specific tissue texture changes and disease progression (see e.g. Nicholson A G, Fulford L G, Colby T V, du Bois R M. The Relationship between Individual Histologic Features and Disease Progression in Idiopathic Pulmonary Fibrosis. American Journal of Respiratory and Critical Care Medicine 166(2) Jul. 15, 2002, https://doi.org/10.1164/rccm.2109039; Ghany M G, Kleiner D E, Alter H, Doo E. Progression of fibrosis in chronic hepatitis C. Gastroenterology, 124 (1) 2003, 97-104; Ruscitti F, Ravanetti F, Essers J, Ridwan Y, et al. Longitudinal assessment of bleomycin-induced lung fibrosis by Micro-C T correlates with histological evaluation in mice; Multidisciplinary Respiratory Medicine 12(8) 2017, https://doi.org/10.1186/s40248-017-0089-0; Adams L A, Sanderson S, Lindor K D, Angulo P, The histological course of nonalcoholic fatty liver disease: a longitudinal study of 103 patients with sequential liver biopsies, Journal of Hepatology, 42 (1) 2005, 132-138).

The list of diseases and conditions that could be diagnosed and monitored by detecting early changes in tissue texture is extensive. It includes bone and joint disease, bone degradation from cancer therapy, diseases marked by fibrotic development and fibrous changes, such as liver, lung, kidney, and cardiac disease, neurologic diseases and conditions, including the various forms of dementia, multiple sclerosis, cerebrovascular disease, and autism, tumor formation marked by the development of angiogenic vasculature, and tissue changes in breast and other cancers (Chundru S, Kalb B, Arif-Tawari H, Sharma P, Costello J, Martin D. MRI of diffuse liver disease: characteristics of acute and chronic diseases. Diagnostic and Interventional Radiology 2014; 20:200-208; Berry D B, You S, Warner J, Frank L R, Chen S, and Ward S R, A 3D Tissue-Printing Approach for Validation of Diffusion Tensor Imaging in Skeletal Muscle, Tissue Engineering: Part A, Volume 00, Number 00, 2017, DOI: 10.1089/ten.tea.2016.0438).

Magnetic Resonance Imaging (MRI) is the diagnostic of choice in a wide range of diseases due to its ability to provide tunable tissue contrast non-invasively and without use of ionizing radiation. However, spatial resolution is limited in MR imaging by patient motion, the resulting degradation of spatial coherence across the measurement limiting the ability to image the fine tissue structures common in most organs in response to disease onset and progression. Even with respiratory and cardiac gating techniques, there is sufficient variation between individual acquisitions to cause loss of spatial phase coherence at the high k-values (short wavelengths) of interest for tissue texture measurements. The finer the texture, the larger the data matrix required, necessitating long acquisition times, which leads to increased motion-induced image blurring. Further, as signal strength varies inversely with k, the higher the required resolution, the lower the signal, making reregistration difficult or impossible.

The historic use of MR imagers as cameras has recently undergone a paradigm shift. Images are now seen as quantitative data for mining rather than just as pictures for qualitative diagnostic interpretation. Quantifying chemical and physical tissue proprieties allows physicians to distinguish between healthy and pathological tissue in an absolute sense, making it easier to objectively compare the results of different exams—both inter-patient, and single-patient follow up studies, for monitoring disease progress. Such quantitative information is more representative of underlying pathology-driven changes at the cellular level than is standard imaging. Gulani et al. MAGNETOM Flash | (65) 2/2016 www.siemens.com/magnetom-world; Carlo Pierpaoli, Quantitative Brain MRI, Topics in Magnetic Resonance Imaging. 21(2):63, April 2010; Shah et al. Radiographics May-June 2011, Volume 31, Issue 3

One of these quantitative techniques converts standard digital medical images into mineable high-dimensional data. This technique, termed "radiomics", is based on the concept that biomedical images contain information that reflects underlying pathophysiology and that this relationship can be revealed via quantitative image analyses that enable extraction of features too small to be discerned in the image. These extracted features can then be combined in databases with other patient/diagnostic data, and AI/machine learning techniques used to extract biomarkers for pathology assessment. Beth Orenstein, Radiology Today, Volume 18, Number 12, page 16.

Biologic tissue texture, the microscopic level variation of tissue morphology and composition, is a parameter of paramount importance in disease diagnosis and prognosis. In radiomics, phenotypic tissue texture is the basic measure on which the diagnostic value of the technique rests. What is extracted from images is a voxel by voxel intensity variation that, though not visible to the human eye, is a digital image texture signature. Though the source of this image texture is unknown, and the data is low SNR and is subject to partial volume effects that limit resolution, research has indicated that it nonetheless contains information on pathology. This measurement of tissue texture by post-processing standard MR images to yield patterns in the image not visible to the naked eye is facilitated by recent increases in computer processing ability and the development of powerful feature extraction/pattern recognition tools.

Tumors exhibit genomic and phenotypic heterogeneity which has diagnostic significance relating to tumor grade and whether the tumor is primary or metastatic—information which determines therapy response. Genomic variability underlies phenotypic variation such as intratumoral spatial variation in the cellularity, angiogenesis, extravascular extracellular matrix, and areas of necrosis—microscopic level variations in biologic tissue texture. Tumors with high intratumoral heterogeneity have been shown to have poorer prognosis, hence tumor heterogeneity is a clinically relevant parameter that could augment standard reporting methods. It is difficult to assess intratumoral heterogeneity with random sampling, such as biopsy as this may not represent the full extent of phenotypic or genetic variation within a tumor. Thus, a non-invasive method of assessing the heterogeneity within a tumor would provide significant clinical benefit, particularly in this age of personalized medicine, to select poor prognosis patients for more intensive therapy. Ganeshan B, Miles K A, Young R C, Chatwin C R (2007), Clin Radiol, 62(8):761-768; Ganeshan B, Abaleke S, Young R C, Chatwin C R, Miles K A (2010) Cancer Imaging, 10:137-143; Miles K A, Ganeshan B, Griffiths M R, Young R C, Chatwin C R (2009) Radiology, 250(2):444-452.

The hypothesis underlying radiomics is that image post-processing has the potential to define microstructural features (textures) that can act as biomarkers yielding a quantitative measurement of intra- and intertumoral heterogeneity—including genomic footprint, an extension of radiomics to "radiogenomics". Radiogenomics relies on correlations between biologic texture obtained from image processing with measured genomic signatures, associations drawn from extensive patient data. Davnall et al. Insights Imaging (2012) 3:573-589 DOI 10.1007/s13244-012-0196-6; Incoronato et al. International Journal of Molecular Sciences, Int. J. Mol. Sci. 2017, 18, 805; doi:10.3390/ijms18040805; Jansen et al. Oncotarget, 8, Vol. 9, (No. 28), pp: 20134-20155.

However, as with medical imaging generally, the textural signatures extracted by radiomics analyses are limited in resolution/sensitivity due to patient motion during acquisition of the image data on which the radiomics analysis is based. Though advanced analytics have the power to extract texture data not visible to the human eye, the extracted data cannot be of any higher resolution or information content than the image being analyzed.

SUMMARY

The disclosure herein provides a method for identifying the chemical species of various textural elements in a targeted region of tissue. A volume of interest (VOI) is selectively excited and a k-encode gradient pulse is applied to induce phase wrap to create a spatial encode for a specific k-value and orientation. The specific k-value is selected based on anticipated texture within the VOI. Multiple sequential samples of the NMR RF signal encoded with the specific k-value are recorded as signal data. The Fourier Transform of the acquired signal data is then taken, wherein for each k-encode, the signal recorded is indicative of the spatial frequency power density at that point in k-space. Each peak in the NMR spectrum is then evaluated, whereby the relative contribution to the texture of tissue in the VOI at a k-value for each chemical species is determined.

BRIEF DESCRIPTION OF THE DRAWINGS

FIG. 5A is an example of one time-resolved signal obtained following excitation of the targeted tissue;

FIG. 5B is the FFT of the signal of FIG. 5A, which is the NMR spectrum for the excited tissue wherein integrating each NMR spectrum peak arising from the different chemical species allows the relative contribution of each to the texture at that k-encode to be determined;

DETAILED DESCRIPTION

Figure 1:
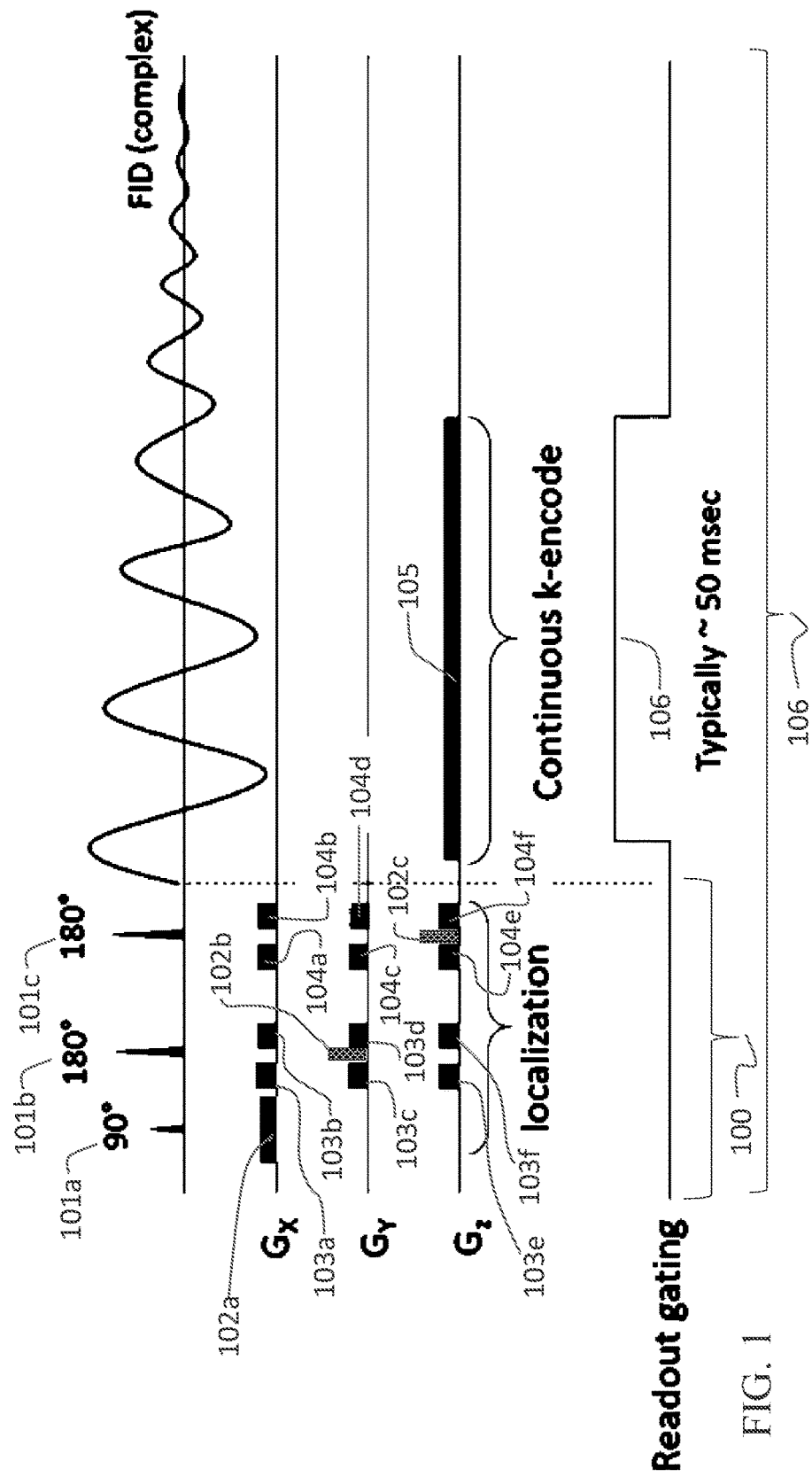
FIG. 1 shows a first variation of the pulse sequence using a selective internal excitation and a continuous encode and simultaneous read of a targeted k-value range, analogous to a commonly used frequency encode but restricted to a targeted range of k-values, at a targeted location in the tissue provided by a series of intersecting slice selective RF/gradient pulses for the selective internal excitation as the VOI.

By novel application of NMR spectroscopy in conjunction with the methods disclosed in parent applications now U.S. Pat. Nos. 9,366,738, 9,664,759 and 9,664,760, the disclosures of which are incorporated herein by reference, the capability of the previously disclosed methods is extended to enable chemical characterization of the targeted tissue texture, thus providing both chemical and spatial microstructrual measurement of the texture, for enhanced diagnostic information and sensitivity.

The method described herein is tolerant of patient motion, thereby enabling measurement of tissue texture to high resolution. Rather than generate an image, tissue texture is evaluated by measuring signal intensity at a discrete set of k-values (textural wavelengths), relevant to a specific disease. This is accomplished by selectively exciting an internal tissue volume as the VOI and applying gradient pulses to phase-encode the VOI at the targeted k-values. The encoded signal from this excited volume is then recorded at each k-encode.

Motion tolerance for measurement of texture is guaranteed both during the time of signal acquisition at each k-value, and from one k-encoded signal acquisition to the next, whether this is within a single excitation, or across multiple excitations. Intra-measurement (within an excitation and associated signal recording) motion tolerance is guaranteed because, once the internal volume is excited, all measures of signal from that volume are coherent—the excited spins simply move with the tissue in the VOI. The lack of need for spatial coherence across excitations provides the inter-excitation motion tolerance when measuring texture rather than an image.

The significant features of the method disclosed herein are: i) definition of a VOI, ii) encoding with a single k-value, iii) a long acquisition period for signal averaging, iv) repeating the sequence with a different k-value. However, the detailed implementation of the sequence is flexible, and it can be applied in a variety of ways, chosen to suit the tissue/pathology under study. For example, multiple k-encoded signals can be acquired over one or multiple TRs. For the description herein the following definitions will be employed: TR—the time between successive excitations in a given VOI, also refers to the time post acquisition during which signal is acquired; and Excitation—the process of exciting an NMR signal, which may include the process of establishing an initial k-encode within the RF and gradient pulses. Acquisition parameters can be chosen to provide the desired contrast to accentuate the specific characteristics of the tissue.

This enhanced method allows data to be acquired over a series of excitations. The wavelength (k-)encode is set before the data is acquired and may or may not be changed during the TR or recording time following an excitation. The pulse sequence will consist of one or a series of excitations: 1) The k-encode can remain constant during one TR enabling multiple acquisitions of signal at a single k-encode; 2) Multiple k-encodes may be employed during one TR, pulsing the gradient at selected time intervals following the initial excitation of the VOI, to achieve the desired set of encodes, recording data with the gradient off; 3) data may be acquired following excitation, with the gradient on, allowing acquisition across a continuous tailored band of k-values within each TR. In this case, data analysis would require accounting for the continuous variation in effective B-field.

Figure 2:
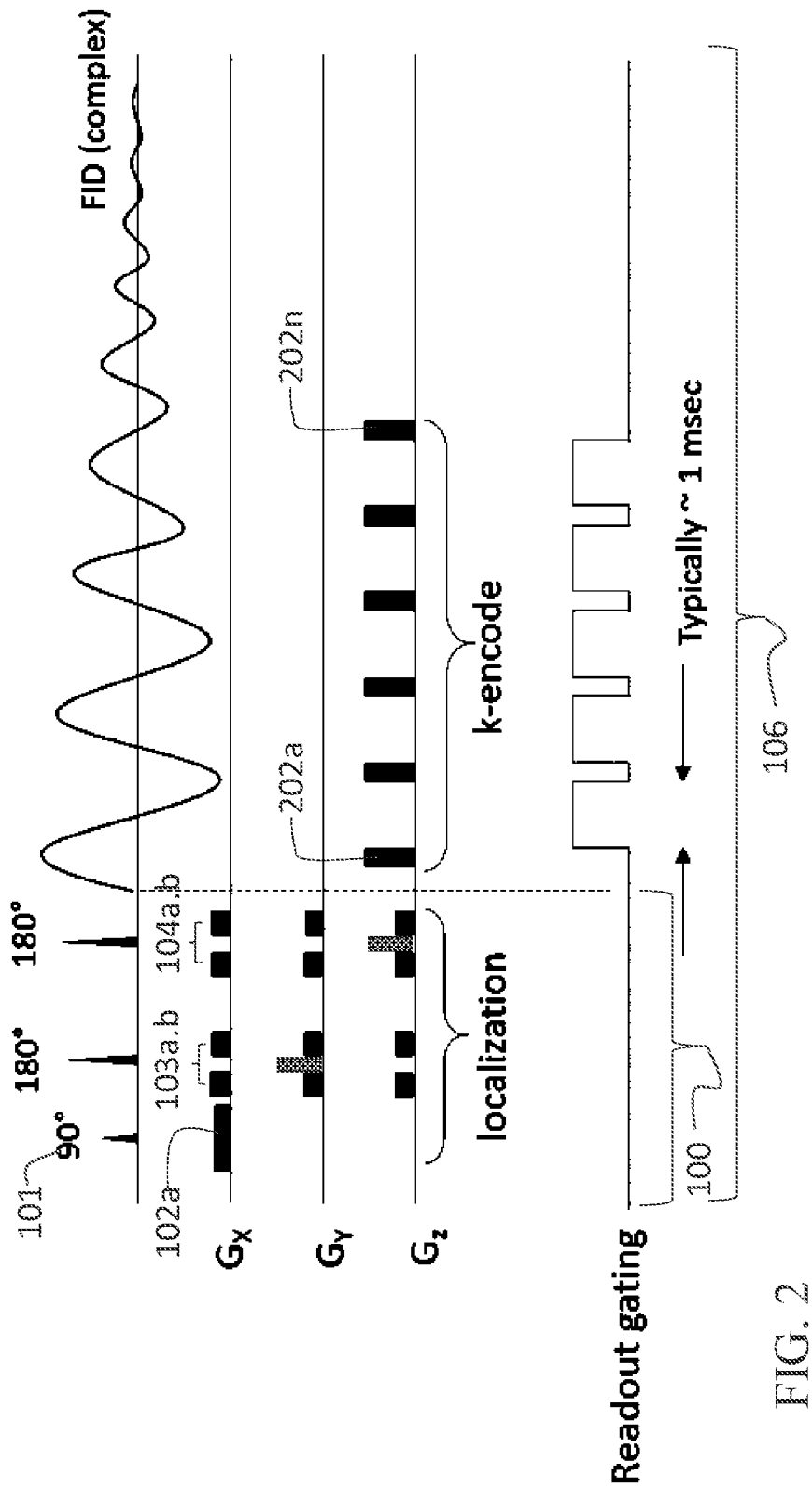
FIG. 2 shows a second possible variation of the pulse sequence, the "Targeted and Discrete Set" which uses a targeted, discrete set of k-values encoded into the sample, with all of the phase-encoding and data acquisition occurring in a single TR.
Figure 3:
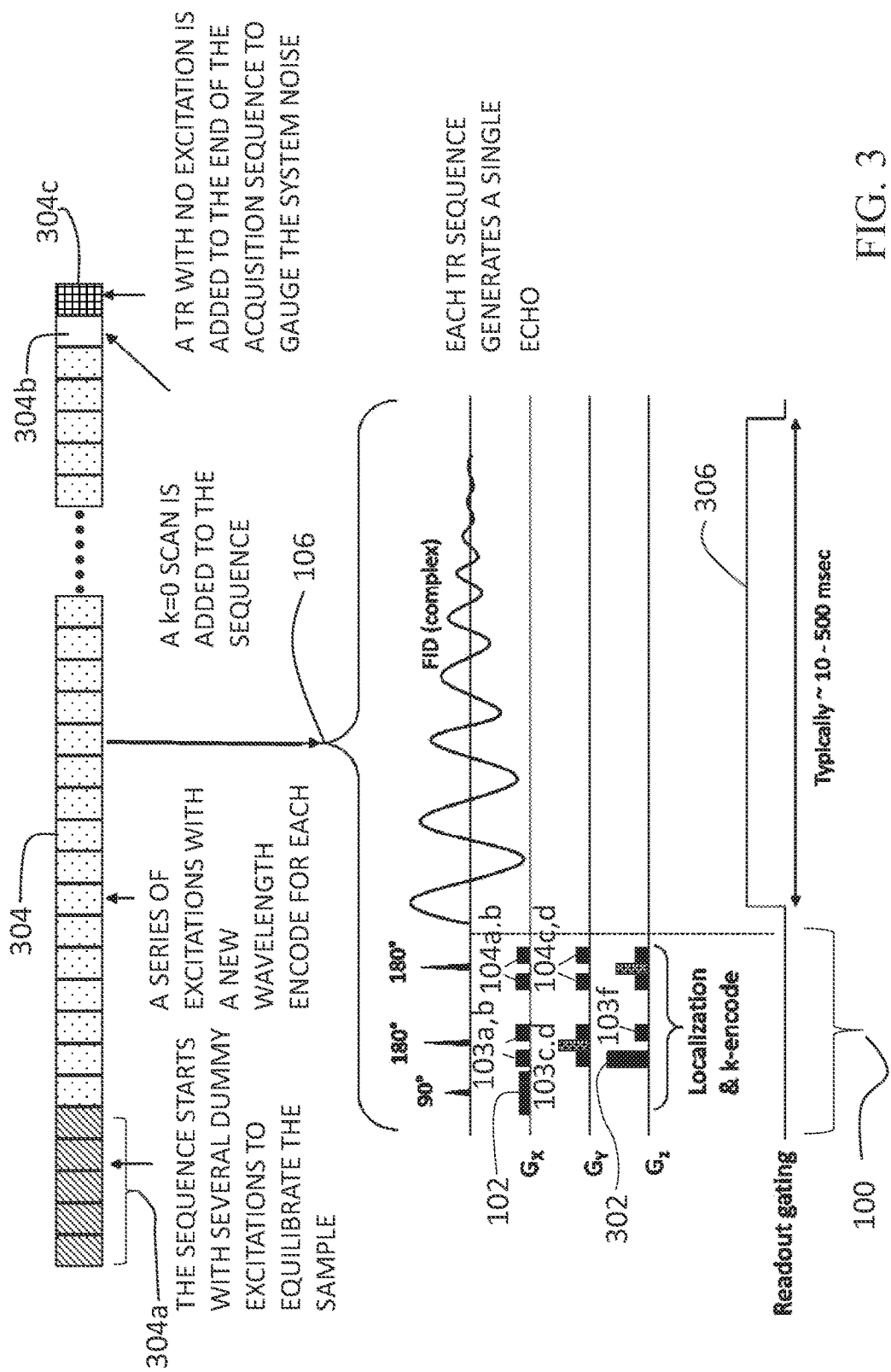
FIG. 3 shows a third implementation of the technology, wherein a single k-value (textural wavelength) is encoded during each excitation sequence; subsequent excitation sequences are encoded with the same or different k-values. The free induction decay (FID) is acquired for the full $T2^*$ period.

Three possible variations of the MR pulse sequence used to implement the method discussed herein are shown in FIGS. 1-3. In all cases a given texture wavelength is probed by applying a phase encode to the selectively excited internal volume and recording the signal.

The first variation of an exemplary pulse sequence uses a selective internal excitation and a continuous encode and simultaneous read of a targeted k-value range, analogous to a commonly used frequency encode but restricted to a targeted range of k-values at a targeted location in the tissue. This "Continuous Scan" method is illustrated in FIG. 1 where an excitation sequence 100 of a series of intersecting slice selective RF/gradient pulses provide the selective internal excitation of the VOI. An RF pulse 101a, slice selection gradients 102a-c, RF refocusing pulse 101b and crusher gradients 103a-103f, second refocusing RF pulse 101c, crusher gradients 104a-104f selectively excite the VOI and establish an initial k-encode. A continuous k-encode 105 is then applied to obtain a selected set of k-values with readout gating 106 during the k-encode pulse. In the example shown, the z-axis, Gz is the texture analysis direction. An exemplary TR 106 is shown for reference.

A second variation of the pulse sequence used in the present method uses a targeted, discrete set of k-values encoded into the sample, with incremental phase-encoding and data acquisition occurring after an excitation sequence, a "Targeted and Discrete Set", as shown in FIG. 2. Following a selective internal volume excitation of the VOI as described above for excitation sequence 100, multiple short k-value encoding gradient pulses 202a-202n, advance the encoding through the targeted set of k-values selected based on anticipated texture induced by the pathology or by other method including characterization across a desired region of k-space. Targeting a few select k-values enables acquiring the signal for several milliseconds per k-value, allowing signal averaging to increase the SNR. Readout gating pulses 204a-204n follow each k-value encoding gradient pulse with all gradients off. Although not used in these examples, there are additional techniques to increase the SNR including: i) refocusing the echo with multiple 180° refocusing RF pulses, and ii) the combination of data collected from multiple excitations by combining the magnitude of the signals for each excitation, without the need to correct/control for patient motion, as each separate textural wavelength measure is independent.

The third implementation of the method, the "Multiple Excitation" method, is shown in FIG. 3. In this implementation with selection of the VOI using RF excitations 101a-c, slice selection gradients 102a-c, crusher gradients 103a-103d and 103f, and 104a-104f, as described for excitation sequence 100 above. A single k-value (textural wavelength) is encoded with gradient 302 during each excitation sequence. Each excitation in a series of excitations encode a k-value. The gating pulse 306 is applied such that the FID is acquired for the full T2* period during each TR 106 and an FFT is applied to the data, as will be described subsequently, to yield chemical species information for each specific k-value (textural-wavelength). Integrating or otherwise quantifying the FFT magnitude over the range of the FFT spectrum corresponding to the chemical shift of the species of interest provides a measure for that species at each textural-wavelength (k-encode). Additional variations to enhance the SNR can also be used in this implementation but are not described here.

The use of phase cycling offers the opportunity to further enhance SNR and reduce artifacts resulting from the excitation sequence. This technique is applied herein by issuing a series of multiple 180 refocusing pulses after the initial excitation sequence 100 and systematically varying the phases of the exciting and refocusing RF pulses to acquire multiple measurements of the spin echo signal within each TR 106. If originally applied, the k-value selection gradients are reapplied after each refocusing pulse for the selected k-values. The resulting signals with common k-values are then combined to reduce or eliminate certain artifacts, for example coherence path artifacts.

As will be described in greater detail subsequently, the Fourier Transform of the time-resolved data record following each TR or excitation produces an NMR spectrum reflecting the chemical species present at the selected k-encode. (If the k-encode is switched part way through signal acquisition, following an excitation, the data records at each of the k-values can be transformed separately to determine the relative contribution of a chemical species at that point in k-space.) The integrated area under the peaks or other quantification in this NMR spectrum is proportional to the contribution of the chemical species to the textural signal at that k-encode. If there is only one peak in the NMR spectrum then there is only one chemical species capable of producing an NMR signal at the encoded k-value. If there are two or more peaks at a single k-encode, then the texture at that specific k-encode/wavelength contains, in proportion, the various chemical species in the spectrum.

At each new excitation, the VOI can either be positioned as close as possible to where it was in the former excitation, or the VOI can be moved to another part of the tissue or anatomy and data acquired there. To build up a spectrum of textural wavelengths at one location in the tissue, it is not necessary to maintain spatial coherence from one excitation to the next. The only requirement for such characterization is that the VOI remain within a region of similar textural signature. Within each excitation placed within a region of similar textural signature, this condition is met because the VOI moves with the tissue if there is any tissue/subject motion. From one excitation to the next, the requirement for VOI positioning is much less stringent than is required in image formation. The requirement that the VOI remain within the region of tissue to be characterized, across multiple acquisitions, can be accomplished by repositioning if the accumulated drift due to motion becomes too large. Again, spatial coherence from one excitation/encode to the next is not required.

Each sequence of excitations may be preceded with a plurality of dummy excitations 304a to equilibrate the sample and followed by a k=0 encoded excitation 304b and a TR with no excitation 304c to gauge system noise.

The two key technical aspects of the described method that enable quantitative assessment of fine textures in the presence of patient motion are: i) motion tolerance and ii) high signal to noise. Additionally, the method enables chemical shift differentiation of texture components, and avoidance of artifacts that arise from a finite analysis length.

Motion tolerance stems from two phenomena, the first is that the coil (antenna) receives signal from everywhere within its field. Provided the displacement is not a large fraction of the antenna field, the encoded tissue signal phase and magnitude will be minimally altered, i.e., the antenna is largely blind to motion of the encoded signal within the antenna field. Additionally, because the protons in the VOI are independent (no substantial coherence or interference effects), and because the proton spin direction is decoupled from the molecular orientation, once excited and encoded, the excited volume of tissue (VOI) can rotate, distort or change direction of motion during the acquisition period without consequence to the signal. This is true as long as the VOI stays within the receiver, and the homogeneous B0, volumes.

The second phenomenon guaranteeing motion tolerance is the fact that, though the patient/VOI might move during the application of a field gradient (e.g. during any of the slice-select gradients, the application of any crusher gradients, or the application of any k-encoding gradients), causing protons in the VOI to incur a phase shift, it is straightforward to show that this phase shift will be small for the size and duration of gradient and likely velocity of the patient. The typical speed of motion for the chest wall during breathing, or tissue motion around a beating heart, is 10-20 mm/s, slow enough that any phase shift is minor. Further, recording in quadrature provides the possibility for post processing. Additionally, this phase shift is common to the whole VOI, so there is no change in the encoded k-value, merely a phase advancement for the VOI as a whole. Since this phase advancement is time dependent, there is an effective frequency shift of the signal, but again it is simple to show that a typical frequency shift will be only a few hundred Hz, well within the front end A/D bandwidth. Since the signal is measured in quadrature, any phase shift with respect to the receiver reference phase will not attenuate the signal.

Inter-measurement motion tolerance (between consecutive excitations) is also guaranteed because the signal power at each k-value is acquired independently of the others—it is not necessary to maintain spatial coherence between the measurement of one k-value and the next (or a repeat measure); all that is needed is that the VOI remain positioned within a region of similar tissue texture.

Rapid tissue motion during the selective VOI excitation will have a minor effect on the fidelity of the boundaries of the VOI. This is likely to be less than that caused by imperfect 180° pulses and does not materially affect the ability to encode and record high k-encoded measures of texture in the VOI.

The described method achieves a significant enhancement of SNR relative to clinical imaging by selecting and focusing on a targeted subset of k-value encodes to characterize the tissue textures in the VOI. Selecting a subset of a −k to +k traditional frequency encode provides the opportunity to dwell on each of the targeted k encodes, in effect sampling them at much narrower receiver bandwidths (<1 kHz). Further SNR enhancement can be achieved by including a series of 180° refocusing pulses to generate multiple spin-echoes. These echoes can be combined to allow a greater degree of signal averaging or analyzed individually to extract the T2 parameters for the signal as an additional chemical signature.

Rather than Fourier transform the power spectrum of signal amplitude vs. k-value into an image, signal power at each textural wavelength is the quantity of interest for this method. Hence, it is possible to accumulate a signal over multiple excitations, for an extended period of tens (or hundreds) of milliseconds, at a single k-value, allowing for a high degree of signal averaging to give strong SNR even for weak signals.

Different chemical species may have different spatial distributions within the tissue and mapping each species as a function of textural-wavelength provides additional diagnostic information. Due to the larger VOIs and extended acquisition times relative to imaging that can be used in the protocol of the disclosed method, there is sufficient signal and bandwidth to measure the NMR spectrum with sufficient resolution to correlate chemical species with the measured tissue texture(s). This is because the resolution is set by the k-encode when there is sufficient signal at that k-value and expanding the length and/or cross section of the VOI enables increasing SNR with no loss of resolution. This technique of simultaneous measure of both the microstructural and chemical species signature of texture may prove to be useful in quantifying inflammation in cases where healthy tissue has its water signal in an organized texture, while in the inflamed state the water may have migrated throughout the tissue and lost its organized texture.

VOI dimensions should be chosen to suit the textural-wavelengths of interest in the sample. In particular, the dimension of the VOI in the analysis direction (z) needs to be sufficiently long to avoid artifacts introduced by the slice select profile that defined the length of the VOI. The VOI should be at least 4 times the maximum wavelength of interest to avoid these artifacts. For measured wavelengths <¼ of the VOI length, the effect is minor.

The optimal choice of textural-wavelengths targeted for measurement will vary for different diseases and pathologies since the signature length-scales for their texture varies. Application to specific diseases will require development of an optimally chosen sparse sampling of k-space. This effort will be significantly informed by the existing histological literature and is anticipated to rely significantly on machine-learning algorithms which will enable correlations to be developed between the textural data and pathology/outcomes. Ultimately, this will result in a library of protocols/parameters tailored to specific diseases. The data output from application of the method discussed herein can be a matrix of k-values vs. relative or absolute intensity, in effect a power spectrum of intensity at the selected range(s) of k-values targeted to a specific pathology. The range may be continuous or sparsely sampled at specific regions in k-space—basically any trajectory through k-space can be selected.

In addition to this output data matrix of relative or absolute intensities in k-space for measure of a specific tissue texture, use of the associated NMR signal from each measurement can be used to identify interleaved textures of different chemical compositions.

Combination of the data acquired using this new technology with the knowledge of the selected acquisition parameters that determine texture contrast, yields important information towards diagnostic assessment of the targeted tissue, and the changes in it that are markers of disease onset and progression. Extraction of information from the acquired data, towards disease assessment, can be maximized by varying the acquisition parameters to generate a range of tissue contrasts, the variation in contrast enabling determination of pathology by elucidating both the morphology and the chemical nature of the tissue texture under study. Towards disease diagnosis, correlation of this acquisition parameter space, with the acquired texture data, can be used to determine biomarkers for disease. This can be done by inspection, however the recent impetus to apply AI algorithms to imaging data can be applied here to great effect, enabling extraction of much more detailed information relating to pathology onset and progression.

The use of AI can take the form of correlation between the output data and various other measures of pathology from a subject. Sufficient correlating data is required to lead to a robust convergence of the data towards diagnostic content, and can enable development of specific biomarkers that, in addition to providing means of tracking disease, facilitate understanding of disease etiology.

Towards extracting maximum information from the acquired data, tissue-based high-resolution data sets can be probed in silico to determine the most useful regions of k-space to analyze towards best assessment of the fabric of the diseased tissue. Further, such modelling can elucidate optimal selection of contrast mechanisms to apply to an in vivo measurement. However, even in cases for which there is little a priori knowledge of a specific tissue texture or how it is affected by disease, tissue texture changes/differences can be assessed by simply acquiring data by this new MR-based technology, in a targeted region of tissue, and correlating it with specific diagnostic measures for the pathology through AI/machine learning. It is not necessary to know a priori a specific textural signature type, or a specific tissue biomarker. Diagnosis can be through AI pattern pattern/feature extraction from the highly structured data set resulting from application of the disclosed method, and comparison to other diagnostic data/outcomes, whether structured or unstructured. This can be done by a combination of supervised and unsupervised learning. By this method, texture pattern markers can be extracted for specific pathologies.

Figure 4:
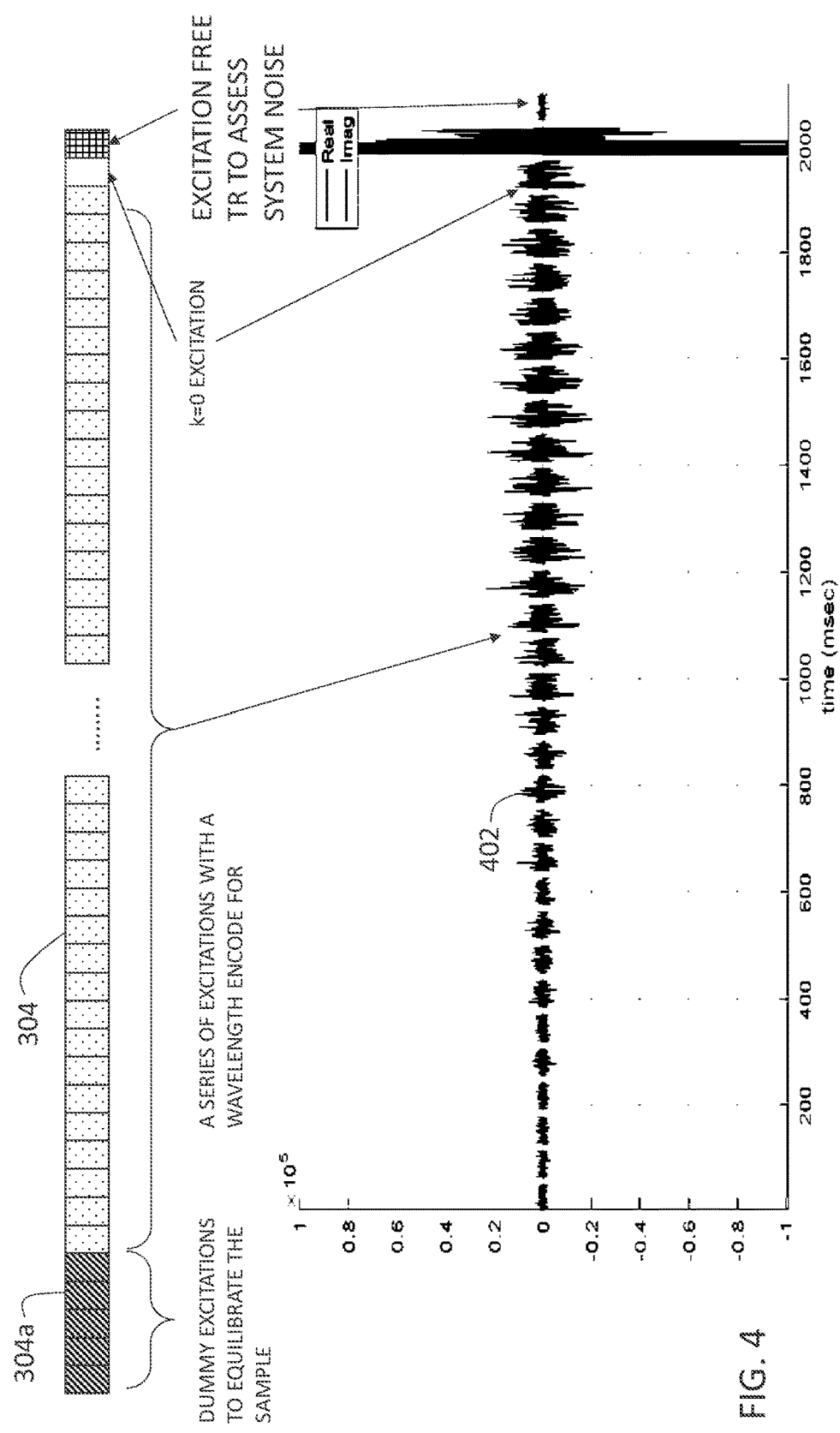
FIG. 4 is a depiction of signal measurement sampled over the course of a series of TR's, each excitation sequence having a k-encode as shown in FIG. 3.

FIG. 4 illustrates data acquisition across a series of excitations 304 (as described with respect to FIG. 3), with a single k-encode at each excitation, the k-encode being varied from one excitation to the next. (The labels in the figure are for a specific exemplary software implementation used for data acquisition.) In practice, the number of repeat acquisitions at a specific k-encode could be selected by SNR considerations at that region in k-space, for the tissue under study. In the simplified case illustrated, the signal 402 resulting from each excitation is recorded by sequential sampling throughout each TR, with a single k-encode per excitation. In actual practice, the TR, TE, and applied gradient profiles would be selected to provide the desired contrast between the textural elements under study and the desired echo profile. As described in application Ser. No. 15/604,465, any type of contrast required to highlight the textural elements may be used in conjunction with the method.

FIGS. 5A and 5B illustrate the signal 502 from a multi-species texture (FIG. 5A), and the NMR spectrum 504 obtained by taking the Fourier Transform of that signal (FIG. 5B). If only one k-encode per excitation is used, the signal recorded in that TR is indicative of the spatial power density at that point in k-space; the NMR spectrum obtained from the Fourier transform of that signal yields the relative contribution of each chemical species in the NMR spectrum to the texture at that point in k-space. This is the case for the acquisition shown in FIG. 5A wherein, at the single k-encode for which the signal was acquired, the structure is comprised of two chemical species, characterized by peaks 506 and 508, as seen in the plot in FIG. 5B, which is the Fourier Transform of the time-resolved signal of FIG. 5A. The relative contribution to the texture at that k-value for each chemical species can then be evaluated by integrating the area under each peak in the NMR spectrum, analyzing the relative width of the peaks or their maximum signal magnitude. Ratioing the integrated value of the area under the peaks may also provide an assessment tool for species determination.

Figure 6:
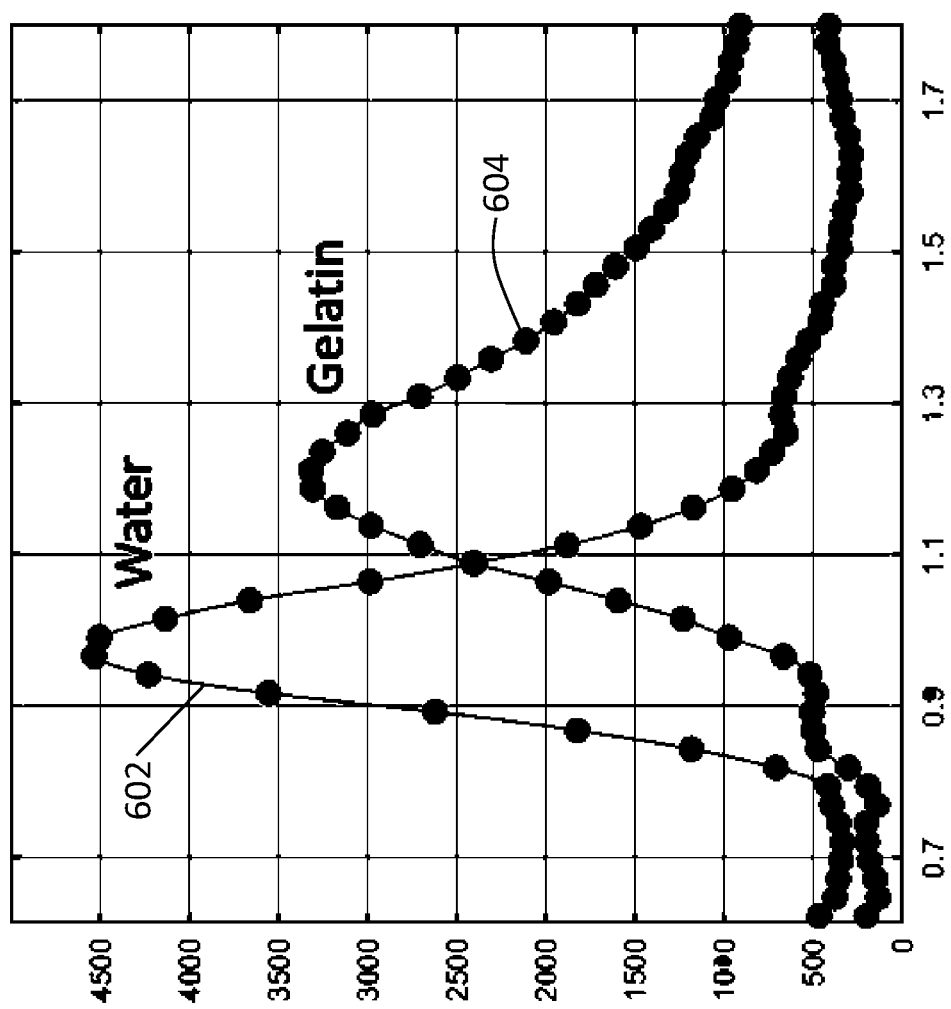
FIG. 6 is a graphical image of water and gelatin texture power vs. wavelength.

By stepping through k-space, in successive excitations, and evaluating 1) the signal magnitude vs. k-encode, and 2) the NMR spectrum at each k-encode, a spectrum of signal power vs. textural wavelength (k-value) can be built up for each separate chemical species, in the tissue region under study as shown for exemplary chemical species in FIG. 6; water 602 and gelatin 604.

Figure 7:
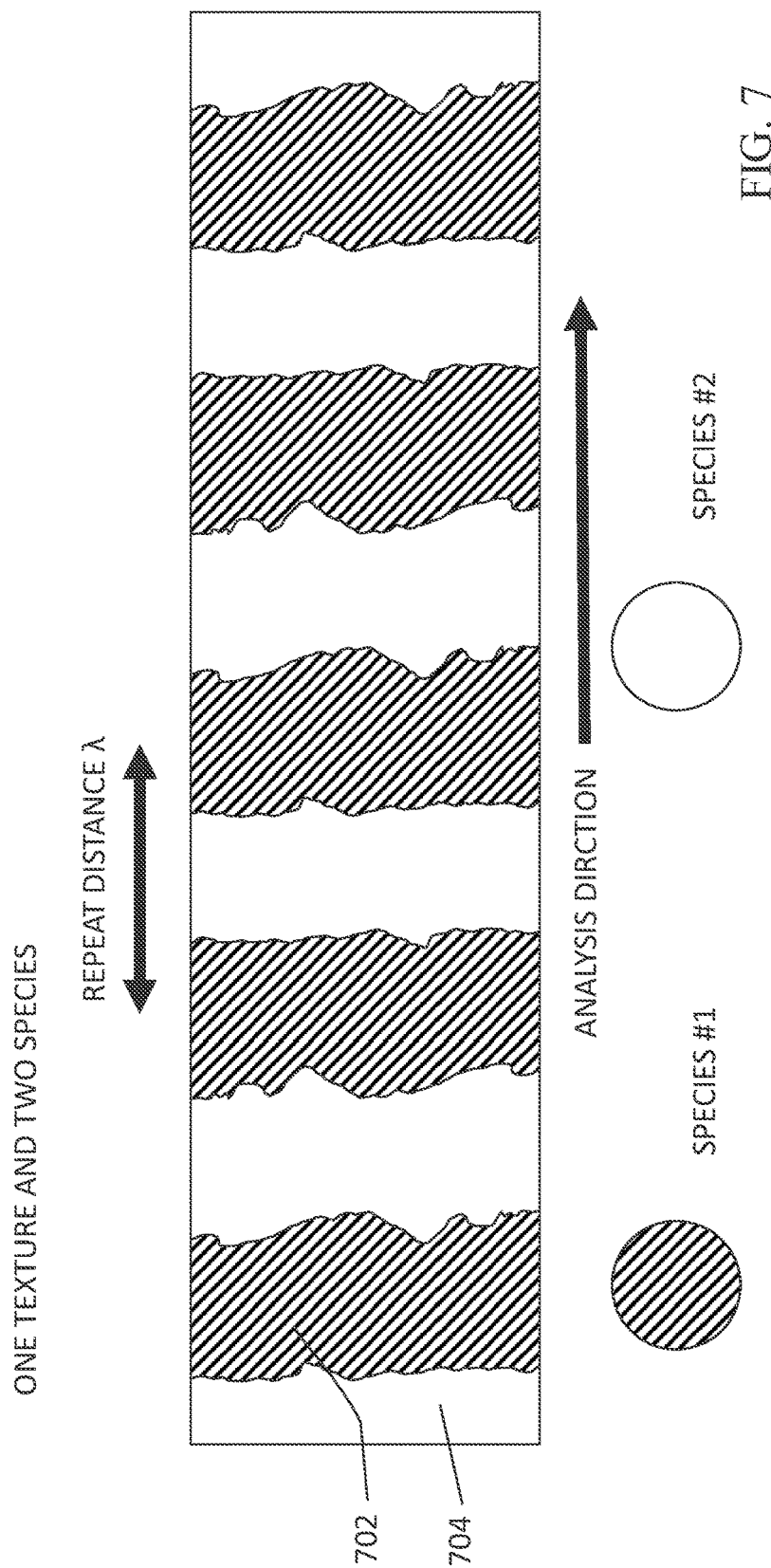
FIG. 7 is a representation of two species having different NMR spectra in a uniform texture; and, FIG. 8 is a representation of three mixed species having differing NMR spectra in a mixed texture.

Two generic situations illustrate application of the disclosed method to separately probe textures composed of differing chemical species. The first case is a sample having a texture made up of two different materials (species 1 and species 2) with different NMR signals with either equal or different magnitude—i.e., one texture in this case with a predominant repeating pattern of wavelength $\lambda$. As an example, FIG. 7 illustrates species 1, 702, and species 2, 704, having different NMR spectra with either equal or differing signal magnitude. A non-NMR specific k-encoded excitation with wavelength $\lambda$ will generate a signal of: (1) Low to zero magnitude if the magnitude of the individual species are equal, or (2) higher magnitude if the magnitudes of the individual species are unequal. Therefore, by separating the signals by NMR frequency (by Fourier transforming the received signal and separately measuring the individual NMR signals, e.g., by calculating the area under the spectral peak, or by measuring the maximum signal), the sensitivity (SNR) to the texture at the encoded k-value can be increased.

Another benefit of separating the signals from each of the two components is clear in the case in which there is infiltration of one species into the other. For example, in the case of myelin rich minicolumns in the cortex of brain tissue, where there is a lipid rich species and a water rich species. When, for example, water infiltrates into, as an example, a lipid rich structure the relative measured magnitudes for the two species of a k-encoded measurement matching the texture wavelength $\lambda$ will change. This is a particularly useful as it enables making in a single excitation/measurement an assessment of the degree of infiltration. An important point is that since it is a single excitation—the measurement for the texture made up of the two species is from identically the same VOI.

A second example is illustrated in FIG. 8. In this case there are three species. K-encoded excitation at a particular wavelength $\lambda$ will suppress signals from textures of different wavelength, e.g. species 1, 892, species 2, 804, and species 3, 806. Additionally, NMR frequency selectivity can be applied to identify and remove signal from other species that may have some signal at that k-value but are not related to the targeted texture exhibited by the target species. Hence using the NMR frequency to identify and suppress species from other textures will increase the SNR of the measurement.

Clinically, the ability to characterize both the microstructural texture (thickness, spacing, variability, anisotropy, and other measures) and also the chemical composition of tissue is of great value in disease diagnosis, prognosis, and therapy design and staging.

Two key technical aspects of the described method that enable quantitative assessment of tissue microstructural textures in the presence of patient motion are: i) motion tolerance and ii) high signal to noise. Additionally, the method enables chemical differentiation of the textural components of the targeted tissue. As the data output from application of the method is a simple matrix of k-value vs. signal intensity vs. NMR spectrum, ease of interface to data analytics is guaranteed. Rather than applying image processing algorithms to post-process standard, low resolution MR images, the method described herein provides a high-information-content, high-resolution, high SNR data input to downstream analytics, facilitating biomarker definition. The measured biomarker values can be used to provide a simple, high sensitivity and specificity quantitative diagnostic score of disease stage to the physician.

The highly-structured, simple data generated by the described method interfaces seamlessly with AI (Artificial Intelligence)/ML (machine learning)-based diagnostics, facilitating AI-based feature extraction for biomarker development, correlation with other metrics to develop surrogate markers for other tissue parameters, and training based on other diagnostic information. The simple functional form of the data obtained from the method described herein—a matrix of chemical shift vs. k-value vs. signal intensity—simplifies application of any downstream analytics. Unsupervised feature extraction/pattern identification is easily accomplished as the initial step in biomarker development. Subsequent supervised training to develop biomarkers can be based on outcomes and/or other disease metrics. Because the described method is an unambiguous, highly structured and simple matrix-based dataset, the transfer function from data acquisition by the method described herein to definitive textural and chemical signature can be developed by correlation with simple physical and tissue phantoms based on ground truth measures. Such correlation ensures unambiguous data interpretation in clinical use. Subsequent training of the resultant features in the data by outcomes and other diagnostic metrics, provides biomarkers relating the underlying physical and chemical properties of the tissue to disease stage.

A recent diagnostic technique aimed at converting MR images to mineable diagnostic data, uses image post-processing to extract features not visible to the naked eye. Pattern recognition algorithms identify features such as tissue textures, for correlation with other patient data, developing correlations and disease models through use of sophisticated bioinformatics. These models then can assist with diagnosis, prognosis, and therapy design. The conversion of images into diagnostic data is motivated by the concept that biomedical images contain information that reflects underlying pathophysiology, and that the relationship between these features and the underlying pathology can be identified via quantitative image analysis. Gillies et al., Radiology Volume 278, number 2, February 2016. A difficulty with this method, known as radiomics, is that as it does not measure tissue texture directly, but rather measures it by post processing of image data, for which resolution is compromised by patient motion. Hence, the ability to extract correlating pathology measures is limited.—no amount of post processing can extract information that isn't in the image. What is needed is a direct, high-resolution measure of disease-induced textural changes in tissue microstructure. Combined with the high-resolution texture measure, measurement of the disease-driven chemical changes in the tissue would then allow assessment of the complementary microstructural and chemical pathology, enabling a sensitive measure of disease onset and response to therapy, as well as the possibility to develop correlations with other disease diagnostics.

The ability, provided by the method described herein, to correlate chemical composition with tissue microstructure may provide clearer understanding of the underlying causes of disease, and hence better prognostication and therapy selection. This ability is especially useful when attempting to type tumors, and to determine tumor boundaries for resection. An important consideration when diagnosing and typing brain tumors is their metabolic, genomic, and textural inhomogeneity. The NMR spectrum and the textural signature from the necrotic core of a high-grade brain tumor is quite different from that at the actively growing rim. Nearly all brain tumors have decreased N-acetyl aspartate (NAA) signals, and often also have increased levels of Choline (Cho), leading to increased Cho/NAA ratios. Horská and Barker, Neuroimaging Clinics North America 2010 August; 20(3): 293-310.

To assist in diagnostic development, NMR is often used for evaluating brain tumor metabolism. However, the size of the voxel required may lead to high partial volume skewing of the measured chemical signature. Glunde and Bhujwalla; Seminar Oncol. 2011 February; 38(1): 26-41. Further, high spatial resolution is unachievable due to low signal level from a small voxel. Additionally, the chemical signature cannot be associated with a sensitive measure of tissue microstructural texture by standard imaging methods. Post processing images does not provide sufficient resolution for this purpose, due to the effects of patient motion.

As an example, recent research applying magnetic resonance relaxometry to assess pathologic changes resulting from traumatic brain injury (TBI) has highlighted the changes in brain white matter that occur even in the case of mild injury. W. Forest, Aunt Minnie, 2 May 2018. Using myelin water fraction, measured by T1 and T2 relaxometry, as a surrogate MRI measure of myelin content, it was found that myelin increases in response to injury and that this remyelination may persist for many months. However, increased myelin alone is not necessarily a good thing. Animal studies have shown that remyelination following mild TBI may result in disorganized and less functional myelin, with the increased myelin forming a type of scar tissue that can cause disorganized signaling in the brain and which can eventually lead to an increased susceptibility to neurodegenerative disorders such as dementia. Hence, definition of pathology progression needs a measure of both morphologic changes in the tissue microtextures, as well as a measure of changing myelin content. However, even with image post processing, the resolution available from MR imaging is not sufficient to track theses changes in tissue texture. But, combining the textural resolution achievable by the method described in US patent U.S. Pat. No. 9,366,738B2, with measure of chemical signature as a function of textural component in the microstructure provides the requisite diagnostic information.

Some biologic textures, such as normal bone, are composed of a microstructural element (cancellous bone) embedded in a tissue matrix (marrow). As such, the tissue texture is defined by the thicknesses and repeat spacings of these two tissue elements. However, more complex biologic tissue textures may be composed of more than two separate chemical components, each chemical component having its own textural contribution to the tissue's composite textural signature in k-space. While the methods defined in the parent applications to the present application highlighted development of contrast between two components—e.g. bone and marrow, liver tissue and collagen, lipid against a higher water tissue matrix—much information can be added to disease diagnosis by correlation of the chemical and microstructural textural components in multi-component tissue structures. By correlating signal intensity at each point/region in k-space arising from the tissue microstructure under study with the chemical signature at that same k-space location, a high-information content description of the tissue is obtained for diagnostic purposes. This correspondence between the microstructural textural and chemical signal contribution to the texture for each component in the composite tissue can be achieved by acquiring NMR data from each VOI at each location in k-space for which textural data is acquired. Several possible applications follow for application of the combined ability to measure both microstructural texture, including in multi-phase structures, and chemical composition variation.

Quantitative T1 and T2 mapping can detect tissue changes in the peritumoral region of tumors that are not visible on conventional MR images. Relaxation values in the peritumoral edema have a heterogeneous pattern within the first 10 mm from the contrast-enhancing portion of the tumor with a gradient in relaxation values from the contrast-enhancing part of the tumor into the peritumoral edema. This may reflect non-visible tumor infiltration into the surrounding tissue, and this information could be useful for the planning of surgery and radiation therapy. Blystad et al. PLOS One; May 23, 2017 However, in multi-component tissue it is difficult to separate the various decay times arising from separate chemical components. In this case also, a high-resolution measure of tissue microstructure/texture combined with the ability to assign a robust chemical composition measure to each textural phase would provide extremely valuable diagnostic data.

With the increasing diagnostic application of quantitative MRI (qMRI), correlations between quantitative values, such as diffusion rates, diffusion anisotropy, tissue relaxation rates, magnetization transfer ratios, shear modulus, etc. are being developed to enable in vivo characterization of disease state. In many pathologies, though qMRI schemes can correlate disease stage with measured tissue parameters, the inability to determine the underlying cause—physical and/or chemical—of the measured parameter makes diagnosis and prognosis more problematic. Distinguishing whether parameter changes are driven by edema, say, rather than inflammation can be difficult, even when using such advanced schemes as magnetization transfer ratio (MTR) mapping. MTR is affected by both changes in the free hydrogen pool (water content) and the bound hydrogen pool (e.g. those bound to proteins and lipids in cellular membranes such as in myelin). Therefore, exact correspondence of magnetization transfer ratio variation with myelin content is not straightforward. More information is needed. But, combining a direct measure of microstructural tissue textures in the targeted region of tissue with an identification of the chemical signature of each tissue phase contributing to the overall tissue texture, enables correlation between the quantitative parameter changes that reflect disease advancement and the underlying cause, a diagnostic measure which, until now, has remained elusive.

The method described herein solves this problem by a direct, high resolution measure of tissue structure. As the resolution obtainable by this method is not defined by the size of the VOI used to sample the tissue, the VOI dimensions can be selected to enable high SNR measure of chemical composition at each k-value for which signal is acquired.

The value of this method can be seen with reference to diagnosing liver disease. Diseased liver tissue may contain, embedded in the liver tissue matrix, lobules of fat reflecting steatosis development, micro-vasculature, identifiable by hemoglobin content, along with the collagen fibrotic development associated with disease progression. Guan Xu, www.nature.com/scientificreports; 4 Feb. 2016. Each constituent chemical phase has a specific textural signature in k-space. The tissue may then be characterized by acquiring data across a range in k-space, using MRS to determine the chemical composition at each k-value. This variation on the invention disclosed in parent U.S. Pat. No. 9,366,738, correlating textural signature with chemical signature, provides valuable additional information towards diagnosis, prognosis and therapy definition.

MR elastography (MRE) uses the increase in tissue stiffness attendant with fibrotic development in liver disease to stage disease. Tissue stiffness is measured from images acquired while acoustic waves pass through the liver. Though providing a good assessment of liver stiffness, this technique is hindered by the difficulty in determining the underlying cause of this pathology. Many factors other than fibrotic development can result in increased stiffness, such as inflammation, biliary obstruction, hepatic congestion, and hepatic venous obstruction. Additionally, iron overload can lead to low signal, making diagnostic interpretation difficult. Low et al. *World Journal of Radiology* 2016 Jan. 28; 8(1): 59-72 ISSN 1949-8470—online.

An ability to measure the disease-induced variations in tissue texture in conjunction with measure of the relative proportion of the various chemical species composing the probed tissue would provide the ability to associate tissue microstructure with specific underlying species infiltration to determine whether the textural changes arise from collagen-based fibrotic development. This ability to track chemical signature across k-space is provided by the invention disclosed herein, by simultaneous measure of chemical signature by NMR, textural location in k-space, and signal amplitude. This enables determination of the extent of fibrotic development using both physical and chemical signatures. Because the resolution of the measure of tissue texture is not determined directly by the size of the VOI used, the VOI can be sized to enable high SNR acquisition of NMR data. Repeat acquisition at a specific k-value within one excitation provides high resolution measure of tissue texture. Hence, the method enables a clinically robust measure of both the component microstructures and chemical species resulting in pathology development.

Due to the robustness and sensitivity of the method, the output data, even upstream from application of analytics, can be used to correlate with pathology for training towards diagnostic assessment. This can be seen with reference to a technique called radiogenomics, an extension of radiomics, which relies on ML analysis of post processed image data to derive genetic signatures of disease. Based on the textural patterns observed in the post-processed image data, training by correlation with genomic fingerprints extracted from the region of a lesion would allow the textural data to be used as an in vivo surrogate of the genomic signatures. While virtually all patients with cancer undergo imaging at some point and often multiple times during their care, not all of them have their disease genomically profiled (nor can afford to test repeatedly). But, as referrals for genomics increase, the ability to compare textural data and genomic data are increasing, leading to development of libraries correlating the textural with the genomic signature.

Textural data obtained by the disclosed method—both microstructural and chemical species—can be used as a surrogate marker for both genomic fingerprint and histologic pathology measure. The correlation between the textural data and genomic and histologic measures can be defined using AI/machine learning techniques. These techniques facilitate extraction of patterns/features from the data obtained by the disclosed method, which can then be trained as biomarkers through correlation with genomic or histologic data obtained from the same tissue regions. Due to the fact that the disclosed method of obtaining textural data is non-invasive, data can be acquired across any organ or tumor, eliminating the sampling errors attendant with use of biopsy-based genomic or histologic measures. This is important because high resolution assessment of tumor heterogeneity—textural, chemical, and genetic—may prove critical in the assessment of tumor aggressiveness and prognosis to help distinguish cancerous from benign tissue, by adding information about cancer type and grade. Each tumor may contain several measurable features describing texture obtained from both the microstructural and chemical textural signatures. These include texture anisotropy, variability, and tissue heterogeneity across the tumor.

Additionally, training of these extracted features against other patient diagnostic information/records/outcomes, enables development of high-sensitivity, non-invasive biomarkers for these diagnostic measures, to assist in disease diagnosis, prognosis and therapy planning.

The data obtained by the method disclosed here is a high-resolution, high-information content measure of tissue texture—both chemical and microstructural/phenotypic. It can be used as a virtual digital biopsy, especially when an actual biopsy is not practical, such as for screening or when repeated assessments of response to therapy are needed. The non-invasive quality of the technique enables longitudinal use in treatment selection and monitoring and application across tumors/organs. As MR data is obtained for almost every patient with cancer, the hurdle to application of the technique is low. Acquisition of the requisite data takes less than a minute using the method disclosed here, so there is little obstacle to the development of databases to facilitate biomarker generation. The method disclosed here provides a powerful means of distinguishing the various causes underlying specific pathology expression. By the ability to track changes in chemical content of tissue, simultaneously associating this chemical content with specific microstructural (textural) components of the overall tissue texture, greatly expands the information in the acquired data. Rather than relying on tissue contrast to determine the chemical components of texture, which is fraught due to the lack of a one to one correspondence between contrast and chemical content, an exact measure of chemical signature at each textural wavelength is obtainable. Now, distinguishing underlying sources for disease response, such as distinguishing edema from inflammation, can be readily achieved—edema is reflected in a steadily increasing water signal in the NMR spectrum, while inflammation is tied to the increasing presence of collagen. Therefore, these two different pathways leading to variation in the biologic texture can be distinguished by the disclosed method. This is just one example of an application of the technique. In all pathologies for which tissue texture is important the combined information on the microstructural and chemical species component(s) of the tissue texture enables more sensitive and specific diagnosis. For instance, the degradation of the neuronal columns in the cortex attendant with cognitive decline is associated with a change in the myelin content of the targeted tissue, as the bundles of neurons degenerate with time. By use of the disclosed method the change in microstructural regularity and width of the neuronal columns can be associated with a variation in myelin content, adding valuable diagnostic information and monitoring of therapy response. Similarly, in development of fibrotic response, such as in liver, lung, kidney, cardiac, and pancreatic disease, to name a few, collagen fibers develop in response to disease progression and are used as the basis of many diagnostic methods. Again, other confounding factors such as inflammation, edema, steatosis, iron-overload, and obstructions, can lead to changes in tissue texture. Ability to determine the chemical species components of each of the separate phases of the pathologic tissue texture would significantly aid in understanding the disease progression and hence setting therapy and monitoring therapy response.

Additionally, the data acquired by both the method disclosed in parent application Ser. No. 15/604,465 and the method described in this disclosure, which extends tissue texture assessment to chemical labelling, provides a simple, high-value, high-information content input to AI/ML analytics. The diagnostic measure of tissue texture described in this disclosure involves acquiring both microstructural and chemical data as a function of texture wavelength (k-value). As such, the data is inherently in a highly ordered format—texture intensity vs. wavelength as one measure and relative intensity of chemical species vs. wavelength as a second measure. This can also be seen as a 3-dimensional plot of k-value vs. intensity, vs. chemical Larmor frequency. While use of AI analytics is often fraught due to difficulty dealing with unstructured data such as electronic health records, audio notes, freehand physician notes, or random data sources, the highly structured form of the data generated by the method described in this disclosure greatly simplifies its input to downstream analytics. Hence, after data acquisition in the MR scanner, the data output is fed into analytics such as a machine learning/deep learning algorithm that will identify salient features/patterns in the data and, based on previous training of the analytics via outcomes or other ground truth, will identify these features as a biomarker for diagnosis of disease state.

Due to its highly-structured format, the data is readily analyzable by existing algorithms for pattern recognition towards biomarker extraction. Further, this is a self-calibrating (intensity at any selected wavelength can be used as an intensity reference), direct measure of texture, which enables development of multiple biomarkers from the tissue texture signature, depending on correlation with texture variability, heterogeneity, anisotropy, number and intensity of species or similar parameters. Because the data input is highly structured, the size of the training set needed for correlation with other markers of disease progression is reduced.

Radiogenomics and radiomics data can be combined with other medical data using bioinformatics. However, the limiting factor is that no amount of image processing can extract information that is not present in the image. As with medical imaging generally, the extracted features are limited in resolution/sensitivity by patient motion. Use of the method described herein provides motion immunity, providing much higher information content data to feed into the downstream analytics, enabling definition of more sensitive, accurate, and robust biomarkers, and hence better correlational prediction of other tissue biomarkers of disease.

This method provides a unique texture measure that can be used to type tissue both in and around tumors with high (previously unachievable) resolution, enabling sensitive assessment of tissue heterogeneity, a marker of tumor type and grade. One of the tissue changes associated with tumor growth is the development of angiogenic vasculature in the region of the tumor. The ability to measure the variation in the microvessels across the tumor region would provide significant diagnostic power in typing the tumor and defining boundaries.

Again, AI/machine learning analytics may be used for feature extraction and biomarker development from the data obtained by application of the disclosed method, for diagnostic purposes and for developing correlation of these biomarkers with other diagnostic metrics, and other measures of tissue texture to enable their use as a surrogate measure of these other metric.

As an example, tumors exhibit genomic and phenotypic heterogeneity which has diagnostic significance relating to tumor grade and whether it is a primary or metastatic tumor. Imaging resolution is not high enough to assess microscopic morphologic heterogeneity on the scale that would provide a high diagnostic value in tumor biology—instead, surrogates such as signal relaxation rate are used. However, the method described herein can readily provide the resolution needed for a direct measurement of phenotype. Further, by varying the underlying contrast mechanism, the method can be used to assess blood flow, myelin, collagen, and other phenotypic features.

Using AI/machine learning analytics to extract features and develop biomarkers from the combination of the microstructural and chemical species texture features identified by the present method for diagnostic purposes allows correlation of the developed biomarkers with other diagnostic metrics, and other measures of tissue texture for use as a surrogate measure of the other diagnostic metrics.

Measurement of absolute intensity on MR images is not possible due to both inter and intra scanner and operator variability, hence there is a push currently to acquisition of quantitative MRI parameters to enable standardization. Parameters such as T1 (decay time), T2 (decay time), PD (proton density), ADC (Apparent Diffusion Coefficient), and FA (Fractional Anisotropy)—tissue-specific quantities that have absolute values independent of scan settings—can be directly compared across scanners, across patients, and longitudinally. Such tissue parameters can then be the basis for definition of quantitative biomarkers of disease. A common presentation of these measurements is by mapping them across regions of interest in the anatomy, as a spatial overlay on a standard MR image. As the method described herein produces an absolute, quantitative localized measurement, which is self-calibrating, it offers a perfect addition to the measurements used in quantitative imaging, one that can be correlated with other data, including standard imaging, at specific locations, while yielding data from microscopic features—a measurement currently unavailable. This, the method described herein provides a direct measure of tissue microstructure that enables correlating variations in other parameters with the direct measure of tissue microstructure and chemical composition provided by the method.

Sensitive measure of tumor molecular and microstructural phenotypic heterogeneity may prove critical in the assessment of tumor aggressiveness and prognosis. Research has already shown the capacity of image-processing texture analyses, and correlation with other diagnostic measures, such as genomic fingerprinting, and outcomes, to help distinguish prostate cancer from benign prostate tissue, or to add information about prostate cancer aggressiveness. Measure of heterogeneity of various tissue attributes has exhibited similar diagnostic benefit in a range of cancers including breast cancer and lung cancer. The method disclosed here enables more robust measure, at much higher resolution and sensitivity, of not only phenotypic tissue textures underlying such measures of heterogeneity and correlation with other measures and outcomes, but now enables identification of the various chemical changes in tissue that contribute to pathology development. This enables much higher diagnostic sensitivity and specificity towards the characterization of tissue heterogeneity, enabling much stronger correlations between the measured and inferred diagnostic parameters, which can then be used to type and grade tumors.

High resolution measure of the combined physical and chemical composition of pathologic tissue texture as provided by the disclosed invention yields highly valuable information towards diagnosis, prognosis, and therapy determination. Tissue texture signatures that can be measured with the disclosed method include quantitative values such as the mean textural spacing, element thickness, anisotropy, structural variability, heterogeneity, variation from region to region etc. All of these measured parameters can be mapped and correlated with quantitative data correlated with the spatial variation in the quantitative data obtained by other quantitative MR techniques such as T1 (decay time), T2 (decay time), PD (proton density), ADC (Apparent Diffusion Coefficient), FA (Fractional Anisotropy)—tissue-specific quantities that have absolute values independent of scan settings. A common presentation of these measurements is by mapping them across regions of interest in the anatomy, as a spatial overlay on a standard MR image, enabling correlation of these quantitative tissue parameters with specific image features. Though T1, T2, MTR, FA are absolute quantities, the underlying cause of the change in these quantities may not be known—i.e. there are multiple reasons, besides fibrotic development, that can increase tissue stiffness. As the method disclosed here produces an absolute, quantitative localized measurement, which is high resolution and self-calibrating, it offers high-diagnostic-information-content towards understanding the pathology underlying the variation in standard quantitative parameters. The ability, provided by the disclosed method, to measure microstructural and chemical tissue properties to high resolution informs understanding of the pathology changes that result in standard quantitative parameter changes associated with disease progression, providing information that can be used not only for therapy prescription, but in design of therapies.

The presently disclosed method indicates directly changes at the micro level changes in microstructure and changes in the chemical composition of the various phases of that microstructure. Hence, using those measurements, either in place of, or as an adjunct to, the quantitative measures provided by T1, T2, MTR, FA greatly improves diagnostic power—the underlying source of changes in these quantitative parameters can better be diagnosed.

Additionally, machine learning training correlating data provided by the current method with genomic data and with histology, can enable data provided by the disclosed method to serve as a surrogate for these other invasive measures. In this way, all data can be taken from the same region of, say, a tumor. This correlation is directly similar to what is done in radiomics and radiogenomics but, instead of using texture of unknown cause derived by image post processing, the high-resolution texture data provided as disclosed herein may be input into the analytics.

A new form of quantitative MR diagnostic is MR fingerprinting (MRF) wherein multiple multiparametric maps are acquired simultaneously to characterize tissue and evaluate pathology. MR acquisition parameters are varied in a pseudo-random way and the temporal evolution of the resulting signal is recorded. By this method, a "fingerprint" of tissue state, unique to that tissue, is obtained. Tissue parameters are determined by comparison of the signal evolution to libraries of such fingerprints that are associated with known tissue parameters. In acquiring the data by this method, there are limits on the resolution of the acquired signals, due to patient motion across the time of acquisition. Adding the method disclosed herein would extend diagnostic and prognostic capability.

By training datasets obtained by the disclosed method against genomic or histologic data, or any other quantitative tissue measures or diagnostic information from the same tissue, the data obtained by the disclosed method can be used as a surrogate for these other diagnostic measures. Though this is very similar to the practice of radiomics, the tissue texture data is obtained directly here, whereas in radiomics the tissue texture data is obtained by post-processing images—a method that results in much lower textural resolution as input to downstream analytics, hence compromising sensitivity. Further, the method disclosed herein provides measure of both the microstructural and chemical species textural signatures of the targeted biologic tissue. The high resolution of the microstructural texture and added information on chemical texture provides a much higher information content measure to inform the correlation with genomics, histology, and other diagnostic measures, significantly enhancing the sensitivity of the surrogate measure.

Genomic data and histologic data measures are invasive, histology especially so. As such, their application is limited, in time and space. Switching to use of a high-sensitivity surrogate enables targeted measure anywhere in the anatomy, as many repeats as desired, limited only by number of times a patient is put in the MR scanner for diagnostic purposes.

Additionally, though the disclosed method can, as described above, be used as a surrogate for many quantitative tissue measures, the combination of these quantitative measures with the information on microstructural and chemical components of tissue texture, obtained by the method disclosed here, provides complementary diagnostic information, while simultaneously building a library of correlation between the textural data and biomarkers and these other methods.

Having now described various embodiments of the invention in detail as required by the patent statutes, those skilled in the art will recognize modifications and substitutions to the specific embodiments disclosed herein. Such modifications are within the scope and intent of the present invention as defined in the following claims.

What is claimed is:

1. A method for identifying the related texture and chemical species in a targeted region of tissue, the method comprising:
    selectively exciting a volume of interest (VOI) and applying a k encode gradient pulse to induce phase wrap to create a spatial encode for a specific k-value and orientation, the specific k-value selected based on anticipated texture within the VOI;
    recording multiple samples of the NMR RF signal encoded with the specific k-value as signal data;
    taking the Fourier Transform of the acquired signal data, wherein for each k-encode, wherein the signal data recorded is indicative of the spatial power density at that point in k-space; and,
    evaluating each peak in the NMR spectrum whereby the relative contribution to texture of tissue in the VOI at a k-value for each chemical species is determined.

2. The method as defined in claim 1 wherein the step of recording multiple sequential samples further comprises:
    initiating a time varying gradient to produce time varying k-value encodes, a resulting k-value set being a subset of that required to produce an image of the VOI;
    simultaneously recording multiple sequential samples of the NMR RF signal encoded with the k-value set as signal data.

3. The method as defined in claim 1 further comprising:
    acquiring signal data across a series of TRs, with a k-encode at each excitation sequence, the k-encode being varied from one excitation sequence to the next creating a k-value set;
    and wherein the step of taking the Fourier Transform of the acquired signal data comprises taking the Fourier Transform of the acquired signal data for each excitation sequence, the signal recorded in that excitation sequence including the spatial frequency density of each chemical species at that point in k-space.

4. The method as defined in claim 1 wherein the step of evaluating each peak comprises integrating the area under each peak.

5. The method as defined in claim 1 wherein the step of evaluating each peak comprises determining signal magnitude of the peak.

6. The method as defined in claim 1 wherein the step of evaluating each peak comprises determining a relative width of each peak.

7. The method as defined in claim 4 further comprising ratioing the integrated areas.

8. The method as defined in claim 3 further comprising:
    applying multiple 180 refocusing pulses within each TR systematically varying the phases of exciting and refocusing RF pulses to acquire multiple measurements of a spin echo signal within each TR; and
    combining signal outputs with common k-value for reduction of artifacts.

9. The method as defined in claim 8 further comprising reapplying the k-value selection gradients for the selected k-values after each refocusing pulse.

10. The method as defined in claim 1 further comprising:
    generating a k-encoded excitation with wavelength λ to produce signal data with low to zero magnitude if the magnitude of the chemical species are equal, or higher magnitude if the magnitudes of the chemical species are unequal;
    separating the signal data by NMR frequency by Fourier transforming the received signal data and separately measuring individual NMR signals by calculating the area under the spectral peak or by measuring the maximum signal to increase sensitivity to the texture at the encoded k-value.

11. The method as defined in claim 1 further comprising:
    generating k-encoded excitation at a particular wavelength λ for a target species to suppress signals from textures of different wavelength from the target species in one or more of the chemical species;
    using NMR frequency to identify and remove signal from other chemical species that may have some signal at the specific k-value but are not related to a targeted texture exhibited by the target species.

12. The method as defined in claim 3 further comprising:
    post processing the signal data to produce a data set of signal vs k-values for k-values in the k-value set, to characterize textural features of tissue in the VOI.

13. The method as defined in claim 12 further comprising:
    correlating the textural features and chemical species with other patient metrics and outcomes;
    inputting the correlated textural features and chemical species as biomarkers to provide disease diagnosis, prognosis and therapy planning.

14. The method as defined in claim 12 further comprising inputting the textural features and chemical species to provide information of chemical composition in conjunction with variation in microstructural tissue changes.

15. The method as defined in claim 12 further comprising:
    using AI/machine learning analytics to extract features and develop biomarkers from changes in microstructure and changes in the chemical composition of the various phases of that microstructure present in the measured textural features of the tissue for diagnostic purposes; and
    correlating the developed biomarkers with other diagnostic metrics, and other measures of tissue texture for use as a surrogate measure of the other diagnostic metrics.

16. The method as defined in claim 12 further comprising:
    using AI/machine learning analytics to extract features and develop biomarkers from changes in microstructure and changes in the chemical composition of the various phases of that microstructure present in the measured textural features of the tissue for diagnostic purposes; and
    correlating the developed biomarkers with genomic data for use as a surrogate measure of genomic fingerprinting in the targeted tissue.

17. The method as defined in claim 12 further comprising:
    using AI/machine learning analytics to extract features and develop biomarkers from changes in microstructure and changes in the chemical composition of the various phases of that microstructure present in the measured textural features of the tissue and correlating a multiplicity of tissue parameters; and
    using the features and biomarkers as a surrogate marker for the tissue parameters.

* * * * *